United States Patent
Rosocha et al.

(10) Patent No.: US 10,017,479 B2
(45) Date of Patent: Jul. 10, 2018

(54) PROCESS TO MAKE NON NUCLEOSIDAL REVERSE TRANSCRIPTASE INHIBITORS (NNRTI) FOR THE TREATMENT OF HIV

(71) Applicant: Gregory Rosocha, Toronto, Ontario (CA)

(72) Inventors: Gregory Rosocha, Toronto (CA); Robert Batey, Toronto (CA)

(*) Notice: Subject to any disclaimer, the term of this patent is extended or adjusted under 35 U.S.C. 154(b) by 104 days.

(21) Appl. No.: 14/890,731

(22) PCT Filed: Aug. 2, 2013

(86) PCT No.: PCT/IB2013/001733
§ 371 (c)(1),
(2) Date: Nov. 12, 2015

(87) PCT Pub. No.: WO2015/015240
PCT Pub. Date: Feb. 5, 2015

(65) Prior Publication Data
US 2016/0130238 A1    May 12, 2016

(51) Int. Cl.
C07D 257/04    (2006.01)
A61K 31/41    (2006.01)
B01J 19/24    (2006.01)

(52) U.S. Cl.
CPC ............ *C07D 257/04* (2013.01); *A61K 31/41* (2013.01); *B01J 19/24* (2013.01); *B01J 2219/00164* (2013.01); *B01J 2219/00166* (2013.01); *B01J 2219/2401* (2013.01)

(58) Field of Classification Search
CPC .................................................... C07D 257/04
See application file for complete search history.

(56) References Cited

U.S. PATENT DOCUMENTS 7,517,998 B2    4/2009    Deroy et al.

FOREIGN PATENT DOCUMENTS

WO    WO2004/050643 A2    6/2004

OTHER PUBLICATIONS

Lee et al, Jul. 2012, Bulletin of the Korean Chemical Society, vol. 33, Issue 7, p. 2385-2388.*
International Preliminary Report on Patentability.
International Search Report.
Written Opinion of the ISA.

* cited by examiner

*Primary Examiner* — Rebecca L Anderson
*Assistant Examiner* — Karen Cheng
(74) *Attorney, Agent, or Firm* — Chumak & Company LLP

(57) ABSTRACT

A chemical process that can form pharmaceutically acceptable medicaments NNRTI's for the treatment of HIV starting from thiotriazole compounds. The chemical process can form thiotetrazoles such as 2-((1-(naphthalen-1-yl)-1H-tetrazol-5-yl)thio)-N-(2-nitrophenyl)actetamide that is. a potent NNRTI with nanomolar activity.

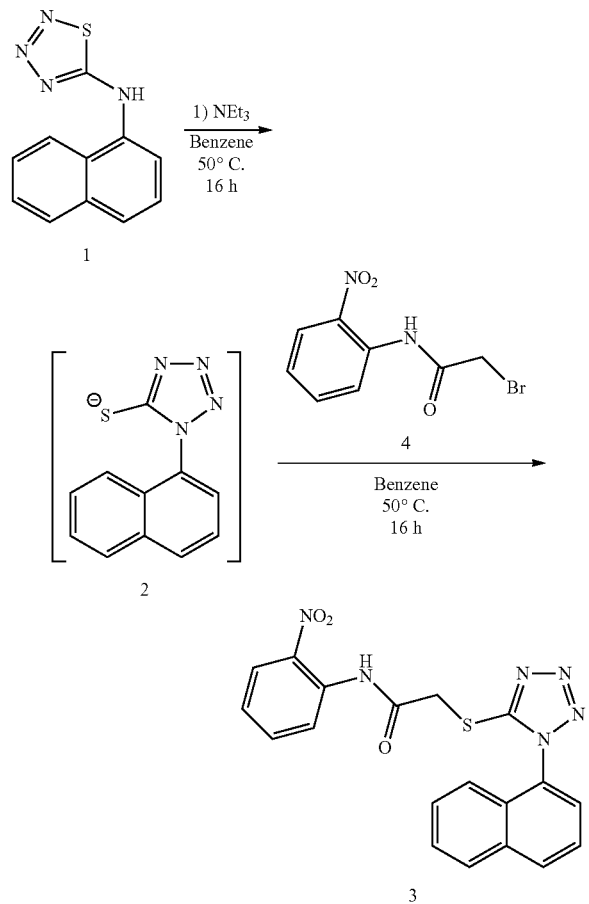

31 Claims, 1 Drawing Sheet

Chemical process to form a NNRTI pharmaceutical compound 3 from 1. The intermediate 2 is trapped by the bromide.
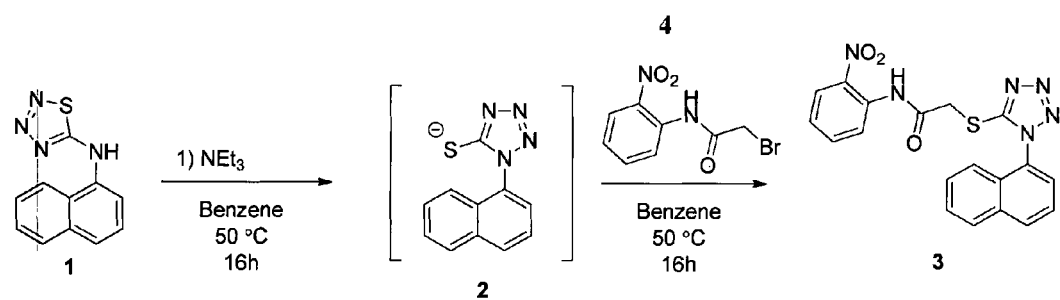

PROCESS TO MAKE NON NUCLEOSIDAL REVERSE TRANSCRIPTASE INHIBITORS (NNRTI) FOR THE TREATMENT OF HIV

The present invention is a new process to synthesize thiotetrazoles that can be used as non nucleosidal reverse transcriptase inhibitors (NNRTI's). The pharmaceutical acceptable salts of the thiotetrazole NNRTI's can be used for the treatment of human immunodeficiency virus (HIV) infection and for the prevention of HIV, in addition as a compliment with other therapies and medicaments used to treat HIV. It is known that compounds that inhibit the function of the HIV Reverse Transcriptase (HIV-RT) can inhibit the replication of the HIV virus in infected cells. Therefore, compounds that can inhibit HIV-RT can be useful for the treatment of HIV and be used for the prevention of contracting HIV. The thiotetrazole analogues made from the process have been shown to have nanomolar activity against HIV. In addition, thiotetrazoles and their pharmaceutical acceptable salts have been proposed to be useful molecules for the development of medicaments that can be used for the treatment of inflammatory arthritis and hyperuricemia. The thiotetrazoles and their pharmaceutical acceptable salts can also be used as research tools to develop new and/or improve current medicaments for the treatment of life altering diseases such as HIV, inflammatory arthritis, and hyperuricaemia.

The process involves the use of thiotriazoles to make a thiotetrazole anion that is trapped in situ by a suitable electrophile to form a thiotetrazole compound. Thiotriazoles are useful molecules and are used as the starting materials in this process because of their stability and safety associated with their use and storage. The thiotriazoles are converted to thiotetrazoles that can be combined with a suitable electrophile to form a molecule that can have therapeutic properties and/or can be used as a research tool to discover new medicaments in the areas of HIV infection and prophylaxis and/or inflammatory arthritis and hyperuricemia.

BRIEF DESCRIPTION OF THE DRAWINGS

FIG. 1 illustrates a chemical process to form a NNRTI pharmaceutical compound.

DETAILED DESCRIPTION

In one embodiment of the present invention, the process involves a solvent such as berzene, a substituted thiotriazole 1, a base, and an electrophile that is trapped when the thiolate anion 2 is formed (FIG. 1). The thiotriazole is stirred in benzene at 60.degree. C. in the presence of triethyl amine for at least 1 h and the electrophile is added and stirred for at least 1-24 hours at 60.degree. C. The reaction is monitored using thin layer chromatography (TLC) or other analytical techniques. When the reaction is complete, the reaction has the solvent removed and is purified using crystallization and/or silica gel chromatography to provide the product 2-((1-(naphthalen-1-yl)-1H-tetrazol-5-yl) thio)-N-(2-nitrophenyl)acetamide in 45% yield which has been shown to be a potent NNRTI with nanomolar activity against the wild type and mutated strains of HIV-1

In a second embodiment of the present invention, the process can use different bromide electrophiles and different thiotriazoles to make different NNRTI analogues that can be used as pharmaceutical preparations to treat HIV which causes Acquired Immunodeficiency Syndrome (AIDS).

In a third embodiment of the present invention is that the process has several advantages over other reported processes. For example, current processes to make thiotetrazole analogues use azides under high temperatures which can be explosive and isothiocyanates which are dangerous mutagens. This process is advantageous because it does not use these azides or For example, 2-((1-(naphthalen-1-yl)-1H-tetrazol-5-yl) thio)-N-(2-nitrophenyl)actamid-e, compound 3 (FIG. 1), can be made by stirring in a batch flask by adding to a stirred solution of the thiatriazole 1 (50.0 mg, 0.219 mmol) in benzene (2.19 mL) and added triethylamine (40.0.mu.L, 0.262 mmol) forming a light yellow mixture. The reaction is then stirred for 18 h and then the bromide (56.0 mg, 0.219 mmol) was added and stirred for an additional 12 h. The reaction progress was monitored using thin layer chromatography and upon completion the reaction was quenched with water (20 mL), and extracted with dichloromethane (3.times.25 mL) and the organic layer dried over Na.sub.2SO.sub.4, filtered and evaporated in vacuo. The crude residue was purified using column chromatography (ethyl acetate in hexanes) to afford the pure product as a light yellow oil (25.0 mg, 45%). IR (Thin film CHCl.sub.3): 3322, 3066, 2924, 2355, 2325, 1701, 1604, 1585, 1498, 1434, 1396, 1341, 1275, 1242, 1149, 1088, 958, 913 cm.sup.-1. .sup.1H NMR (400 MHz, CDCl.sub.3): 11.0 (1H, s, broad), 8.70 (1H, dd, J=8.0, 1.0 Hz), 8.41 (1H, dd, J=8.0, 1.0 Hz), 8.15 (1H, m), 8.01 (1H, dd, J=8.0, 1.0 Hz), 7.54-7.52 (5H, m), 7.47 (1H, d, J=8.0 Hz), 7.42 (1H, m), 4.28 (2H, s) ppm. .sup.13CNMR (400 MHz CDCl.sub.6): 165.6, 156.1, 155.4, 136.0, 134.5, 134.0, 132.2, 129.0, 128.8, 128.7, 127.8, 126.0, 125.3, 124.4, 122.8, 128.8, 128.7, 122.0, 37.4 ppm. MS (EI) m/e (rel intensity): 407 (100), 243 (3), 230 (2), 213 (5), 211 (2), 186 (1), 169 (11), 139 (3) 113 (1) C.sub.19H.sub.15N.sub.5O.sub.3S. HRMS (EI) m/e C.sub.19H, .sub.5N.sub.5O.sub.3S calc'd mass=407.0926, found=407.0920. Further, Thiotetrazole 1 can be made according to the following procedure. For example, N-(Naphthalen-1-yl)-1,2,3,4-thiatriazol-5-amine 1 was made using the general method for thiatriazole synthesis and the crude residue was purified using silica gel chromatography (10-30% ethyl acetate in hexanes) affording the pure thiatriazole 1 as a light tan solid (1.20 g, 75%, mp=122.degree. C.). IR (Thin film CHCl.sub.3): 3391, 3046, 2986, 1550, 1499, 1470, 1424, 1351, 1263, 1220, 1155, 1118, 1050, 894, 741, 703 cm.sup.-1. .sup.1H NMR (400 MHz, CDCl.sub.3): 11.2 (1H, s, broad), 8.12 (1H, m), 8.04 (1H, dd, J=7.5, 1.0 Hz), 7.99 (1H, m), 7.84 (1H, d, J=7.5 Hz), 7.64-7.56 (3H, m) ppm. .sup.13C NMR (400 MHz, DMSO-d6): 177.5, 136.6, 134.6, 129.1, 127.3, 127.3, 127.0, 126.6, 126.6, 122.4, 119.1 ppm. MS (EI) m/e (rel intensity): 228 (4), 187 (6), 185 (100), 169 (12), 158 (17), 153 (26), 141 (22), 127 (86), 92 (6), 75 (5), 62 (2). HRMS (EI) m/e C.sub.11H.sub.8N.sub.4S calc'd mass=228.0470, found=228.0475.

Thiol 2 was made using the following procedure. To make 1-(Naphthalen-1-yl)-1H-tetrazole-5-thiol 2, a stirred 50° C. solution of the napthyl triazole 1 (50.0 mg, 0.219 mmol) in benzene (2.19 mL) was added triethylamine (39.0 μL, 0.285 mmol). The reaction was stirred at 50° C. for 22 h and the quenched with water (25.0 mL) and ethyl acetate (50.0 mL), washed with 1M HCl (3×20 mL), water (3×20 mL) and brine (3×20 mL). The organic phase was dried over sodium sulfate and evaporated in vacuo to afford 2 as white light pink crystals (70.0 mg, 100% yield, mp=120-122° C.). IR (Thin film CHCl$_3$): 3046, 2986, 1499, 1470, 1424, 1351, 1263, 1220, 1155, 1118, 1050, 894, 741, 703 cm$^{-1}$. $^1$H NMR (400 MHz, DMSO-d$^6$): 8.21 (1H, d, J=8.0 Hz), 8.01 (1H, d, J=8.0 hz), 7.79-7.55 (4H, m) 7.39 (1H, d, J=8.5 Hz) ppm. $^{13}$C NMR (400 MHz, DMSO-d$_6$): 134.6, 132.0, 129.6, 129.0, 128.8, 128.3, 127.4, 126.4, 125.3, 122.2 ppm (missing 1 carbon). MS (ESI+) m/e (rel intensity): 229 (90), 228 (4), 227 (2), 217 (3), 213 (2), 212 (14), 204 (3), 201 (100), 200 (5), 197 (4), 187 (4), 186 (6), 185 (2). HRMS (ESI) m/e C$_{11}$H$_9$N$_4$S calc'd mass=229.05479, found=229.05525.

The 2-Bromo-N-(2-nitrophenyl)acetamide 4, was made by adding to a stirred solution of o-nitro aniline (462.0 g, 2.52 mmol) in chloroform (25.0 mL) was added bromo acetyl bromide (242.0 µL, 2.77 mmol) dropwise forming a yellow precipitate. The reaction was stirred at room temperature for 12 h, then quenched with water (75 mL) and extracted with dichloromethane (3×50 mL). The organic washings were dried with sodium sulfate, filtered and evaporated in vacuo to afford a light brown solid (391.0 mg, 51%). In the case that full consumption of the aniline was not achieved, the crude material was reacted again with bromoacetyl bromide allowing for complete conversion of nitro aniline into the amide product. In this case purification was not necessary because of the high purity obtained and the quantitative yield with respect to the nitro aniline. $^1$H NMR (400 MHz, Toluene-d$_8$): 11.2 (1H, s, broad), 8.74 (1H, d, J=8.0 Hz), 8.26 (1H, d, J=8.0 Hz), 7.71 (1H, t, J=8.0 Hz), 7.27 (1H, t, J=8.0 Hz) ppm. $^{13}$C NMR (400 MHz, CDCl$_3$): 165.1, 136.1, 134.0, 126.1, 124.4, 122.2, 29.6 ppm.

The NNRTI 3, has been found to have nanomolar activity against the wild type strains of HIV. In a fourth embodiment of the present invention, the process is also useful for other bromides, R—Br, R=o-nitro phenyl acetamide
 m-nitro phenyl acetamide
 p-nitro phenyl acetamide
 o-methyl phenyl acetamide
 m-methyl phenyl acetamide
 p-methyl phenyl acetamide
 o-chloro phenyl acetamide
 m-chloro phenyl acetamide
 p-chloro phenyl acetamide In a fifth embodiment of the present invention, the process can use other suitable thiotriazoles that have an alkyl, or aryl, or heteroaryl group attached at the C1 position of the thiotriazole ring.

The invention claimed is:

1. A chemical process-consisting essentially of reacting a benzene, a N-napthyl substituted thiotriazole, a triethyl amine, and a bromide electrophile (R—Br), where R is selected from the group containing: o-nitro phenyl acetamide, m-nitro phenyl acetamide, p-nitro phenyl acetamide, o-methyl phenyl acetamide, m-methyl phenyl acetamide, p-methyl phenyl acetamide, o-chloro phenyl acetamide, m-chloro phenyl acetamide, and p-chloro phenyl acetamide to form thiotetrazoles.

2. The chemical process of claim 1 wherein the thiotetrazoles are non-nucleosidal reverse transcriptase inhibitors (NNRTI).

3. The chemical process of claim 1 wherein the reacting step comprises an electrocyclization reaction that forms a thiolate that is trapped by the bromide electrophile in situ.

4. The chemical process of claim 1 wherein the reaction is carried out in 1 step.

5. The chemical process of claim 1 wherein the reaction is carried out in 2 steps.

6. The chemical process of claim 1 wherein the thiotetrazoles are formed after heating to at least 50° C.

7. The chemical process of claim 1 wherein the thiotetrazoles are non-nucleosidal reverse transcriptase inhibitors (NNRTI) that have inhibitory concentrations in the range of gram (g) to nanogram (ng) or Mole to nanomole (nm).

8. The chemical process of claim 1 wherein the reaction is performed using a method selected from one of: a non-continuous method and a continuous method.

9. The chemical process of claim 8 wherein the method is a non-continuous method which is performed in a batch vessel that can be sealed.

10. The chemical process of claim 9 wherein the vessel holds an inert atmosphere.

11. The chemical process of claim 10 wherein the inert atmosphere is a noble gas.

12. The chemical process of claim 8 wherein the method is a continuous method performed in a micro flow reaction vessel comprising pre-fabricated channels and/or grooves with dimensions ranging from 0.100 micrometers to 200 micrometers.

13. The chemical process of claim 12 wherein chemical reaction solvent or fluid passes inside the channels and/or grooves with distances travelled by the fluid ranging from 1 cm to 1000 meters.

14. The chemical process of claim 12 wherein the reaction vessel is capable of obtaining temperature ranges from −150° C. to 400° C.

15. The chemical process of claim 12 wherein the reaction vessel adjusts and regulates the rate of reaction fluid flow and the residence times within the channels and/or grooves.

16. The chemical process of claim 15 wherein the rate of reaction fluid flow is within the range of 0.0001000 mL/minute-500.00 L/minute.

17. The chemical process of claim 15 wherein the residence times are within the ranges of 0.00001 seconds-100 hours.

18. The chemical process of claim 1 wherein the yield of thiotetrazoles is at least 1%.

19. The chemical process of claim 1 wherein the yield of thiotetrazoles is at least 9%.

20. The chemical process of claim 1 wherein the yield of thiotetrazoles is at least 19%.

21. The chemical process of claim 1 wherein the yield of thiotetrazoles is at least 29%.

22. The chemical process of claim 1 wherein the yield of thiotetrazoles is at least 39%.

23. The chemical process of claim 1 wherein the yield of thiotetrazoles is at least 49%.

24. The chemical process of claim 1 wherein the yield of thiotetrazoles is at least 59%.

25. The chemical process of claim 1 wherein the yield of thiotetrazoles is at least 69%.

26. The chemical process of claim 1 wherein the yield of thiotetrazoles is at least 79%.

27. The chemical process of claim 1 wherein the yield of thiotetrazoles is at least 89%.

28. The chemical process of claim 1 wherein the yield of thiotetrazoles is at least 99%.

29. A chemical process that uses a solvent, an amine base, an-N-napthalene substituted thiotriazole and a reaction vessel to make a thiotetrazole comprising the steps of:
 a) mixing the solvent and thiotriazole for any period of time,
 b) adding the amine base into the reaction vessel and mixing for a period of time,
 c) adding a bromide electrophile, and d) heating the reaction vessel to a temperature between the range of 50° C. and 150° C. for a period of time greater than 12 hours.

30. The chemical process of claim 29 wherein the amine base is triethyl amine.

31. The chemical process of claim 29 wherein the reaction vessel is selected from one of: a batch reactor and a micro flow reactor.

* * * * *